United States Patent [19]

Santioemmo et al.

[11] Patent Number: 5,780,385
[45] Date of Patent: Jul. 14, 1998

[54] FELINE URINARY TRACT DISEASE-DETECTING PAPER CAT LITTER AND METHOD

[75] Inventors: Carl V. Santioemmo, Highland Heights, Ohio; James P. Humphries, Frisco, Tex.

[73] Assignee: Ranpak Corp., Concord Township, Ohio

[21] Appl. No.: 444,956

[22] Filed: May 19, 1995

Related U.S. Application Data

[60] Division of Ser. No. 345,524, Nov. 28, 1994, and a continuation-in-part of Ser. No. 153,360, Nov. 16, 1993, abandoned which is a continuation-in-part of PCT/US93/11085 Nov. 19, 1993, and Ser. No. 125,310, Sep. 22, 1993, abandoned, said Ser. No. 345,524, is a continuation-in-part of Ser. No. 153,360, Nov. 16, 1993, abandoned, and Ser. No. 153,491, Nov. 17, 1993, and Ser. No. 125,310, Sep. 22, 1993, abandoned, said Ser. No. 153,360, is a continuation-in-part of Ser. No. 861,225, Mar. 31, 1992, abandoned, said Ser. No. 153,491, is a continuation-in-part of Ser. No. 861,225, Mar. 31, 1992, abandoned.

[51] Int. Cl.$^6$ ........................................ B01J 20/22
[52] U.S. Cl. ........................ 502/401; 119/172; 422/56; 436/66; 436/163
[58] Field of Search ............... 119/171–173, 28, 119/28.5, 706; 422/56, 57, 69, 68.1; 502/150, 151, 401; 436/66, 163

[56] References Cited

U.S. PATENT DOCUMENTS

| | | | |
|---|---|---|---|
| Re. 30,424 | 11/1980 | Heldenbrand | 119/170 |
| 3,059,615 | 10/1962 | Kuceski et al. | |
| 3,154,052 | 10/1964 | Sweeney | |
| 3,581,977 | 6/1971 | Kirsky et al. | |
| 3,626,899 | 12/1971 | Spellman | 119/169 |
| 3,752,121 | 8/1973 | Brazzell | 119/169 |
| 3,828,731 | 8/1974 | White | 119/170 |
| 3,886,901 | 6/1975 | Zeitter | |
| 3,921,581 | 11/1975 | Brewer | |
| 3,978,818 | 9/1976 | Heldenbrand | 119/170 |
| 4,157,696 | 6/1979 | Carlberg | 119/172 |
| 4,172,123 | 10/1979 | Lowicki | |
| 4,275,684 | 6/1981 | Krämer et al. | |
| 4,305,345 | 12/1981 | Otoguro | |
| 4,326,481 | 4/1982 | Gruss | 119/171 |
| 4,341,180 | 7/1982 | Cortigene et al. | 119/172 |
| 4,376,422 | 3/1983 | Whitehead et al. | 119/172 |
| 4,407,960 | 10/1983 | Tratnyek | 436/1 |
| 4,454,055 | 6/1984 | Richman et al. | 252/194 |
| 4,487,163 | 12/1984 | Jobert | 119/166 |
| 4,509,457 | 4/1985 | Durbye | 119/173 |
| 4,532,890 | 8/1985 | Ohki et al. | 119/172 |
| 4,553,671 | 11/1985 | Cheesman | |
| 4,560,527 | 12/1985 | Harke et al. | |
| 4,628,863 | 12/1986 | Eichenauer | |
| 4,736,706 | 4/1988 | Lang | 119/173 |
| 4,774,907 | 10/1988 | Yananton | 119/169 |
| 4,776,300 | 10/1988 | Braddock | |
| 4,782,788 | 11/1988 | Arcand | |
| 4,846,103 | 7/1989 | Brown | |
| 4,890,576 | 1/1990 | James | |
| 4,931,139 | 6/1990 | Phillips | 119/172 |
| 4,938,957 | 7/1990 | Iwahashi | 424/76.21 |
| 4,940,016 | 7/1990 | Heath | |
| 4,957,063 | 9/1990 | Heitfeld et al. | 119/172 |
| 5,018,482 | 5/1991 | Stanislowski et al. | 119/173 |
| 5,031,578 | 7/1991 | Hammons | 119/167 |
| 5,055,520 | 10/1991 | Michael | 119/172 |
| 5,078,099 | 1/1992 | Balson | |
| 5,080,043 | 1/1992 | Fields | |
| 5,081,040 | 1/1992 | Patel et al. | 422/57 |
| 5,082,563 | 1/1992 | Webb et al. | 210/631 |
| 5,088,972 | 2/1992 | Parker | 493/352 |
| 5,097,799 | 3/1992 | Heitfeld et al. | 119/172 |
| 5,117,781 | 6/1992 | Roach | |
| 5,134,013 | 7/1992 | Parker | 428/182 |
| 5,143,023 | 9/1992 | Kuhns | 119/173 |
| 5,144,914 | 9/1992 | Giannakopoulos | |

(List continued on next page.)

FOREIGN PATENT DOCUMENTS

| | | |
|---|---|---|
| 0363292 | 4/1990 | European Pat. Off. |
| 3809635 | 1/1991 | Germany |
| 2247818 | 3/1992 | United Kingdom |
| 2 261 586 | 5/1993 | United Kingdom |
| 8203151 | 9/1982 | WIPO |
| WO 88/00434 | 1/1988 | WIPO |
| 8908387 | 9/1989 | WIPO |

OTHER PUBLICATIONS

Pinney, Chris C., The Urinary System, in Illustrated Veterinary Guide, pp. 425–431, date unknown.

Finco, D.B. and Barsanti, J.A. Role of Diet in Feline Urologic Syndrome, in Current Veterinary Therapy, pp. 1112–1114, date unknown.

The Alphabet Soup of Cat Diseases, in Medicine and Disease, pp. 179–180, date unknown.

Norsworthy, G.D., Feline Urologic Systems, Chapter 40, source unknown, pp. 369–378, date unknown.

Normal Renal Function and Urine Parameters, in Current Veterinary Therapy, p. 1213, date unknown.

Properties of and Excretion Products in Urine: Mammals Other Than Man, in Biology Data Book, date unknown.

*Primary Examiner*—Jill Warden
*Assistant Examiner*—Alexander Markoff
*Attorney, Agent, or Firm*—Renner, Otto, Boisselle & Sklar, P.L.L.

[57] ABSTRACT

A cat litter which comprises a plurality of lightweight, resilient paper strips treated with a pH-indicator and/or an occult blood indicator and folded transversely into generally zig-zag shapes, enables early detection of feline urological syndrome. When wetted with alkaline urine secreted by the cat, the paper strips treated with pH indicator exhibit a noticeable color change. When wetted with cat urine containing occult or gross blood, the paper strips treated with occult blood indicator exhibit a noticeable color change. A mixture of pH indicator treated strips and occult blood indicator strips in the cat litter enables the detection of both alkaline pH and occult blood in the same urine sample. The color changes are easily visible to the observer without requiring unsanitary contact with the cat litter.

14 Claims, 4 Drawing Sheets

U.S. PATENT DOCUMENTS

| | | | |
|---|---|---|---|
| 5,173,352 | 12/1992 | Parker | 428/174 |
| 5,195,465 | 3/1993 | Webb et al. | 119/172 |
| 5,203,282 | 4/1993 | Hasiuk . | |
| 5,209,186 | 5/1993 | Dewing . | |
| 5,267,532 | 12/1993 | Franklin et al. | 119/173 |
| 5,318,894 | 6/1994 | Pugia | 435/28 |
| 5,359,960 | 11/1994 | Yananton | 119/165 |
| 5,362,633 | 11/1994 | Pugia | 435/28 |
| 5,371,054 | 12/1994 | Pluta et al. | 119/173 |
| 5,403,259 | 4/1995 | Parker . | |
| 5,482,007 | 1/1996 | Kumlin | 119/169 |

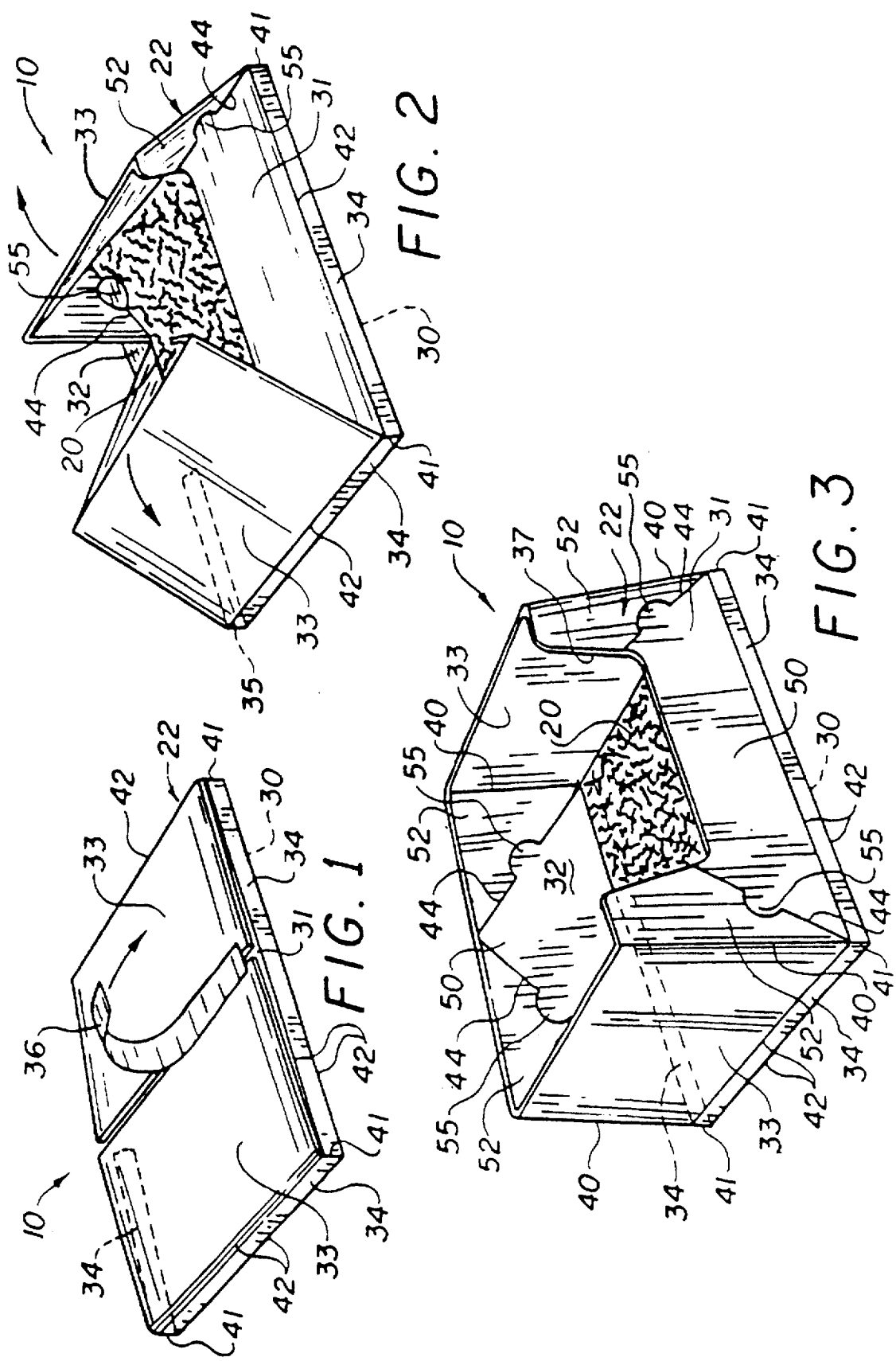

FELINE URINARY TRACT DISEASE-DETECTING PAPER CAT LITTER AND METHOD

RELATED APPLICATIONS

This application is a division of application Ser. No. 08/345,524 filed Nov. 28, 1994 and a continuation-in-part application Ser. No. 08/153,360 filed Nov. 16, 1993 abandoned and a continuation-in-part application Ser. No. 08/125,310 filed Sep. 22, 1993, now abandoned, and a continuation-in-part of PCT/US93/11085 filed Nov. 19, 1993.

Application Ser. No. 08/345,524 is a continuation-in-part application Ser. No. 08/153,360 filed Nov. 16, 1993 abandoned and a continuation-in-part of application Ser. No. 08/153,491 filed Nov. 17, 1993 and a continuation-in-part application Ser. No. 08/125,310 filed Sep. 22, 1993, now abandoned, and a continuation-in-part of PCT/US93/11085 filed Nov. 19, 1993.

PCT/US93/11085 is a continuation-in part of application Ser. No. 08/125,310 filed Sep. 22, 1993, now abandoned.

Application Ser. No. 08/153,360 is a continuation-in-part of application Ser. No. 07/861,225 filed Mar. 31, 1992, now abandoned.

Application Ser. No. 08/153,491 is a continuation-in-part of application Ser. No. 07/861,225 filed Mar. 31, 1992, now abandoned.

The entire disclosures of these prior applications are hereby incorporated by reference herein.

FIELD OF THE INVENTION

This invention relates generally to a cat litter, and more particularly to a resilient paper cat litter and method for detecting feline diseases which are indicated by a predetermined characteristic of the cat's urine, such as a particular pH range and/or blood in the cat's urine. Feline diseases which may be thus detected include feline urinary tract diseases, such as feline urological syndrome ("FUS") or feline lower urinary tract disease ("FLUTD"), and/or cystisis (bladder infection).

BACKGROUND OF THE INVENTION

FUS is a term used to describe a group of clinical signs and symptoms associated with diseases of the urinary tract of male and female cats. Manifestations of FUS include frequent trips to the litter box, straining to urinate with little result, blood in the urine (particularly occult or microscopic blood in the early stages of the disease), urination in inappropriate places, and even pain during urination. The cat may also pace, lick itself, and cry.

The manifestations of FUS are often the result of the formation of mineral crystals, usually struvite, in the cat's urine. Struvite crystals are generally comprised of a magnesium ammonium phosphate complex. While some of these crystals may be passed, accumulation of the crystals can occur in the cat's bladder and urethra, resulting in irritation of the lining of the bladder and urethral walls, making them more prone to bacterial infection and microscopic bleeding. Infection adds cellular debris to the crystal mix and may cause a blockage of the urinary tubes, particularly in male cats. Due to anatomic differences, primarily the smaller diameter of the urinary tubes in male cats, the urinary tract of an afflicted male cat can become completely blocked. The blocked cat may stop eating, vomit and become increasingly agitated. Most worrisome, the condition is immediately life-threatening. If a blocked cat does not receive emergency medical attention to relieve the blockage, the cat may die, in a matter of hours, from uremic poisoning and kidney failure.

Unfortunately, FUS is far too common. As many as 10% of all feline admissions into a veterinary hospital are related to FUS. Most typically, FUS has been observed in overweight cats that have been spayed or neutered, and are between 2–6 years of age.

It has been observed that the struvite crystals associated with FUS, which may lead to fatal blockage, generally form in more alkaline cat urine. Consequently, a diet which causes the cat to excrete alkaline urine predisposes the cat to FUS. In addition, a dietary excess of magnesium and phosphorus will generally magnify the problem, presumably by supplying the minerals needed to form struvite crystals in alkaline urine. Hence, FUS can sometimes be avoided by switching to a premium brand of cat food formulated to generate a slightly acidic urine and which has a relatively low magnesium and phosphorous content.

Regrettably, however, cat owners frequently mistake the initial symptoms of FUS for other problems, particularly constipation. To the owner, the cat's frequent trips to the litter box (where the cat may sit for longer periods of time) indicates that the cat is constipated. Because the cat generally does not have a fever, and appears otherwise normal, at least in the initial stages of the disease, the owner too often assumes that the problem will pass. Even if the cat cries out in pain, the cat owner may not realize that a life threatening condition is imminent. Consequently, there is a need for cat owners to be able to easily monitor their cats' urine for the early signs of FUS, including the presence of an alkaline pH and/or occult blood. (In contrast to red gross or frank blood, occult blood cannot be visually detected by the cat owner.)

Moreover, once a cat has been afflicted with FUS, the cat frequently becomes more susceptible to recurrence of the disease, even after diagnosis and treatment with a diet formulated to generate a more acidic urine. Owners of such cats need to be alerted to the continuing signs of FUS, which can include occult or frank blood in the urine. In addition, blood in the urine can be a sign of other feline diseases, such as cystitis. Consequently, a convenient method of detecting blood in the cat's urine can also alert the cat owner to the presence of such other diseases, thereby ensuring that the cat gets prompt medical treatment.

As can be readily appreciated, however, it is difficult—if not impossible—to get a cat to "give a sample" in which a pH- or blood-detecting test stick could be dipped. As can also be appreciated, particularly by cat owners, it would not be desirable to collect the cat urine in the litter box for testing. For example, replacing conventional litter (e.g. a processed, granular clay) with a material that does not absorb urine might permit a test stick to be dipped into the urine while it was still in the litter box; but the cat owner would then be confronted with a messy testing and disposal problem, particularly if frequent monitoring was sought. Moreover, it would be difficult for the cat owner to avoid unsanitary contact with the used cat litter, a contact made more particularly undesirable if the urine is contaminated by bacteria from a bladder infection.

Alternatively, the cat owner might be provided with a product to be added to conventional, used litter. Such a product would react to the presence of an alkaline pH or occult blood in the urine by undergoing a color change, for example. This approach, however, would be time-consuming and inconvenient, and would again expose the cat owner to the risk of unsanitary contact with the used litter. Further, any color changes which might occur would be very difficult to see when such a product is added to conventional litter, e.g., clay, which already has a bluish hue and turns even darker when wetted. Moreover, the cat owner would still confront the other problems associated with conventional cat litter, including its heavy weight, which makes transport of the litter difficult, and the task of filling and cleaning the litter box. In addition, due to its "non-resilient" nature, large and bulky packaging arrangements are required to accommodate the desired volume of conventional litter.

The drawbacks of the foregoing proposals would only be multiplied in situations outside the home where a large number of cats need to be monitored; for example, in a pet shop, animal shelter and/or at a veterinarian's office. Accordingly, there remains a need for an inexpensive means for routinely and readily monitoring cat urine for signs of FUS, cystitis and/or other feline diseases which are indicated by a predetermined characteristic of the cat's urine, such as a particular pH range and/or blood in the urine. There also remains a need for a detection method which is convenient, easy to use, and acceptable to both the cat and its caregiver.

SUMMARY OF THE INVENTION

The present invention provides a cat litter comprising a light-weight, resilient paper product, which permits the cat owner or care giver to detect feline diseases that are indicated by a predetermined characteristic of the cat's urine. The cat litter comprises a plurality of longitudinal paper strips, folded transversely into generally zig-zag shapes. The paper strips are treated with a chemical indicator selected to exhibit a noticeable color change when the treated paper strips are wetted with cat urine having the predetermined characteristic of the feline disease.

By observing color changes in the cat litter, the cat owner can be readily alerted to the warning sign(s) of the disease. Critical remedial action, such as a change in diet and/or an immediate visit to the veterinarian, can then be taken by the cat owner.

Further, due to the zig-zag shapes of the paper strips, the litter is porous and resilient and can be compressed and then allowed to relax or expand repeatedly. Hence, relatively large volumes can be compacted into small and/or light-weight packages, which are convenient and easy to use and carry. Also, the paper strips can be allowed to relax or expand in an intertwining and interlocking manner, thereby combining to form substantially a mass. The interlocking and intertwining of the paper strips also prevents the cat from dragging pieces of the cat litter out of its box, thereby keeping the cat owner's home in a tidier condition.

The invention is particularly suited to detect FUS, conveniently and inexpensively, even in its early stages and/or for the post-diagnosis monitoring of cats with a history of FUS. When used to detect FUS, the paper strips preferably comprise bleached, white Kraft paper, and have preferably been treated with a pH indicator and/or an occult blood-indicator.

The pH indicator is selected to exhibit a marked color change when the treated paper is exposed to alkaline cat urine. Preferred examples include bromocresol purple, phenol red, and chlorophenol red.

Similarly, the occult blood indicator is selected to exhibit a marked color change when the treated paper is exposed to cat urine comprising occult blood and/or its by-products (e.g., hemoglobin). The occult blood indicator preferably comprises guaiac, benzidine, ortho-tolidine, ortho-dianisidine, or other leuco-dyes, which produce a blue color in the presence of microscopic blood and hemoglobin.

The cat litter preferably comprises a mixture of strips treated with the pH indicator and strips treated with the blood indicator. The indicators are preferably selected to undergo different color changes when exposed to an alkaline pH or occult blood in the urine, respectively. Then, when the cat uses the litter, the owner can readily determine simultaneously if the cat's urine is alkaline and/or contains blood.

Moreover, the presence of blood can alert the cat owner to the possible presence of cystitis or other feline diseases. In addition, gross red blood in the urine (another warning signal of feline disease) can be easily observed by the cat owner, particularly when the treated paper strips are manufactured from white Kraft paper.

The cat litter may also be treated with a sizing, in an amount sufficient to permit the urine to roll off the strips initially to the bottom of the cat litter, when the cat wets from the top of the litter. Then, the urine is more gradually absorbed by the strips, allowing them to become wetted from the bottom upwards. Consequently, the cat can be kept drier and more comfortable, thereby further encouraging use of the litter.

In addition, the paper cat litter is biodegradable and thereby environmentally responsible, particularly when used in connection with a disposable container, as hereinafter described. In the present invention, the walls of the disposable container are preferably coated with a biodegradable, water-repellant and urine-resistant material. In addition, an absorbent paper sheet treated with an antibacterial and/or anti-odor substance is preferably placed under the treated paper strips, at the bottom of the container.

The present invention also provides a method for detecting feline diseases, particularly FUS, in a cat, which are indicated by a predetermined characteristic of the cat's urine. In this method, a web of paper material is treated with a chemical indicator selected to exhibit a marked color change when wetted by cat urine having the predetermined characteristic. The treated paper is longitudinally cut into a plurality of paper strips, which are folded transversely into generally zig-zag shapes.

The method is preferably employed to detect FUS. In this preferred embodiment, the method comprises treating the paper strips with a pH indicator and/or occult blood indicator, selected to exhibit a marked color change upon contact with alkaline cat urine and/or bloody urine, respectively.

These and other features of the invention are fully described and particularly pointed out in the claims. However, the particular embodiments depicted and exemplified are only illustrative of the range of ways by which the principles of the invention may be employed.

BRIEF DESCRIPTION OF THE DRAWINGS

In the drawings:

FIG. 1 is a perspective view of a disposable cat litter box containing an embodiment of the resilient, paper cat litter of the invention, wherein the cat litter box includes a container which is convertible between closed and open conditions in which it respectively forms a closed and open receptacle, the container being shown in the open condition;

FIG. 2 is a perspective view of the cat litter box of FIG. 1, with the container being shown in a partially opened condition;

FIG. 3 is a perspective view of the cat litter box of FIG. 1, with the container being shown in the closed condition;

DETAILED DESCRIPTION OF THE INVENTION

Figure 4:
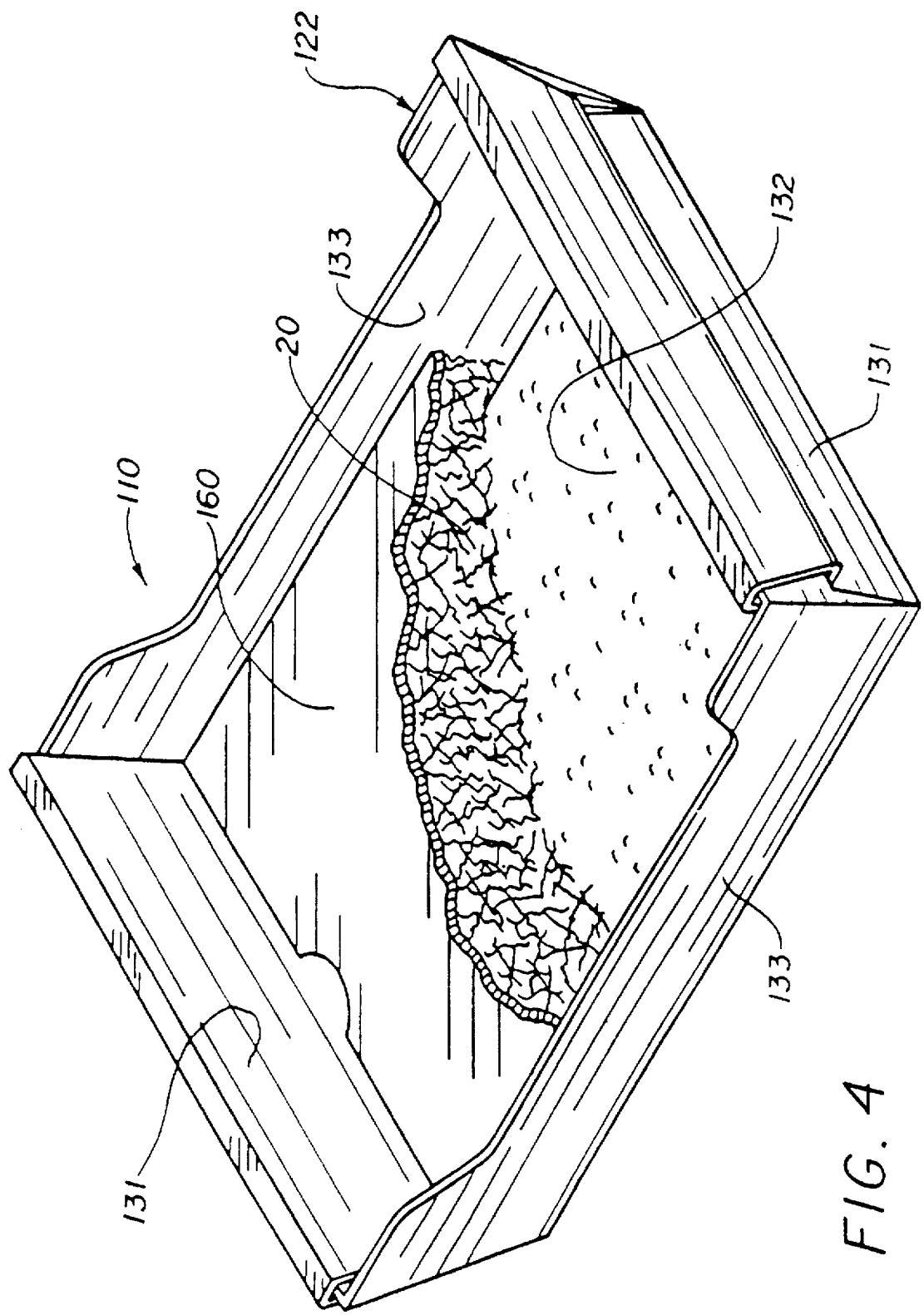
FIG. 4 is a partially cut-away perspective view of a different cat litter box containing the resilient paper cat litter of the invention, wherein the cat litter box includes a flat cover panel enclosing the cat litter, and in which cat litter box the cat litter is underlain by an absorbent sheet of paper product that has been treated with an antibacterial and/or anti-odor substance.

Referring now to the drawings in detail and initially to FIGS. 1, 2, 4, 5, and 6, the feline disease detecting cat litter 20 of the present invention is exemplified. As illustrated and described in further detail herein, the cat litter 20 is preferably packaged and used in a disposable cat litter box 10 which is convertible between closed and open conditions. These preferred cat litter boxes are disclosed in U.S. patent application Ser. No. 08/125,310 and/or PCT Patent Application No. PCT/US93/11085, both of which have previously been incorporated by reference herein. However, it is also contemplated that the cat litter 20 can be packaged and used with other cat litter boxes and packaging materials.

In accordance with the invention, the cat litter comprises a resilient paper product, which comprises a plurality of longitudinal paper strips. The strips have been folded transversely into generally zig-zag shapes, and treated with a chemical indicator selected to undergo a marked color change when the treated paper strips are wetted with cat urine having a predetermined sign or characteristic of the feline disease.

When used to detect FUS, the paper is preferably treated with a pH indicator and/or an occult blood indicator. More preferably, the cat litter comprises a mixture of pH- indicating and occult blood-indicating paper strips. The cat litter may also comprise a mixture of treated strips and untreated strips.

The pH indicator is selected so that the treated strips exhibit a noticeable color change when wetted with alkaline cat urine, which is one of the primarily early warning signals of FUS. Upon observing the color change, the cat owner can take prompt remedial action, such as a change in diet and/or a visit to the veterinarian, thereby averting serious illness or even death of the cat. (By selecting a pH indicator which changes color in acidic cat urine, the present invention can also be used to detect other feline diseases, which are known to be characterized by acidic cat urine).

Normal cat urine has a pH value ranging between about 5.5 to about 6.6. Therefore, the selected pH indicator preferably exhibits a prominent color change at or above a selected pH value of about 6.8. Preferred pH indicators include bromocresol purple, which rapidly changes from yellow in acidic solutions to purple in alkaline solutions, over a pH range of 5.2 to 6.8; chlorophenol red, which rapidly changes from yellow (acid) to red (alkaline), over a pH range of 5.2 to 6.8; and phenol red, which also rapidly changes from yellow (acid) to red (alkaline), over a pH range of 6.6 to 8.0.

The occult blood indicator is selected to exhibit a marked color change in the presence of occult blood. Preferred indicators comprise guaiac, benzidine, ortho-tolidine, orthodianisidine, or other "leuco-dyes," which turn various shades and intensities of blue, in the presence of occult blood, hemoglobin, or other peroxidase-containing blood components. (The peroxidase catalyzes the oxidation of the leuco-dye by peroxide, resulting in the color change.)

The strips comprising the cat litter are formed from a paper material. Preferably, the strips are made from thirty pound Kraft paper, which preferably comprises bleached white Kraft paper. It is contemplated, however, that other paper materials can be used, provided that the material does not resist treatment with the selected indicator, and is absorptive to cat urine. Also, when treated with the selected indicator, the strips must undergo a noticeable color change when wetted with cat urine having the predetermined sign(s) of the feline disease.

Further, the paper material should be biodegradable, and thus environmentally responsible. Moreover, it should be light-weight so as to provide a cat litter which can be easily carried and used. Preferably, the paper material is selected to provide a cat litter having a density of between about 0.01 to about 0.100 ounces per cubic inch and more preferably a density of approximately 0.035 inches per cubic feet when compressed as when packaged in a cat litter container.

In addition, it should be recognized that the paper material for forming the strips includes a natural resilience with a tendency to remain in a straightened form and to resist folding or bending. This principle can be readily observed by simply taking a small sheet of Kraft paper and folding it in half. Initially, when pressure is applied, the two halves of the sheet between the fold are pressed together in close contact. When the pressure is released, however, the fold has a tendency to relax or expand, thereby causing the halves to angularly separate.

Due to the foregoing characteristics, the paper strips, when folded transversely into zig-zag shapes, act like mini-springs, which can be longitudinally compressed and allowed to relax or expand repeatedly. Hence, relatively large volumes of the cat litter 20 of the present invention can be compacted into small and/or light-weight packages, which can be conveniently transported and stored. This feature provides an additional significant benefit to the manufacturer, dealers, and users of the cat litter of this invention.

Moreover, when allowed to relax or expand, the resilient zig-zags can become intermixed and repositioned in an intertwining and interlocking manner. Preferably, when the cat litter is in use, the strips have been permitted to intertwine and interlock sufficiently to form substantially a mass. The interlocking and intertwining prevents the cat from dragging pieces of the cat litter out of its box, thereby keeping the cat owner's home in a tidier condition.

Examples of suitable machines/methods for converting a continuous web of paper material into the plurality of zig-zag shaped strips comprising the cat litter of the present invention are disclosed in U.S. Pat. Nos. 5,088,972; 5,134,013 and 5,173,352; and U.S. patent application Ser. Nos. 07/861,225, 07/971,046, and 08/153,360. (All of these patents/applications are assigned to the assignee of the present invention, and have been previously or are hereby incorporated herein.) In these machines/methods, a portion of the continuous web of paper material is withdrawn and cut into a plurality of strips by rotating sets of cutting discs, thereby forming a body of such strips. The plurality of strips are advanced against a restricting means acting on the body of strips in such a manner that the natural resilience of the paper causes the paper strips to be folded into generally zig-zag shapes, with substantially uniform adjacent and opposite planar portions between the folds.

Using the preferred machines/methods, the tightness of the resulting folds can be controlled by adjusting the speed at which the strips advance against the restricting means. A slower speed generates a tighter fold or crimp. Applicants have observed that tighter folds permit the zig-zag strips to become more thoroughly interlocked and intertwined. Thus, the speed can be regulated to provide a cat litter having the desired degree of interlocking and intertwining.

The continuous web of paper material employed is commonly supplied in a compact form, such as roll. Alternatively, as is disclosed in pending U.S. application Ser. No. 07/994,940 (assigned to the assignee of the present invention), the disclosure of which is hereby incorporated by reference herein, the web of paper material could be fan-folded into a rectangular stack.

The machine/method for converting the web of paper material into the zig-zag strips preferably incorporates a system for treating the paper with the selected indicator. Examples of suitable machines/methods for treating the paper strips with the indicator are disclosed in pending U.S. application Ser. No. 08/153,360, previously incorporated herein. The preferred treatment method comprises providing a continuous web of an untreated paper material; withdrawing a portion of the web to thereby form a withdrawn portion; applying the indicator in liquid phase to the withdrawn portion of the paper material; and converting the treated withdrawn portion into the plurality of zig-zag shaped strips. The preferred treatment-applying device preferably includes a container or trough which contains the indicator in the liquid phase, a roller which is partially submerged within the liquid treatment and which contacts the withdrawn portion, and a drive assembly which rotates the roller and thereby transfers the liquid treatment from the container to the withdrawn portion.

The drive assembly of the preferred treatment system may include an adjustment mechanism which selectively varies the rotational speed of the roller for selectively varying the amount of the liquid treatment being transferred to the withdrawn portion. The speed can then be adjusted as needed to treat the paper web with the indicator for a time period sufficient to ensure that the resulting cat litter produces a noticeable color change when later wetted with cat urine having the predetermined characteristic of the feline disease. Also, the rotational speed of the roller can be controlled to ensure that the paper web does not become so moistened that it loses its integrity or turns "mushy", thereby precluding the paper from being folded into resilient zig-zag shapes.

The pH indicator, when applied in liquid form, preferably comprises an aqueous solution. The indicator can be added to water (or another liquid base) in either powdered or solution form. Suitable powdered or liquid forms of phenol red, chlorophenol red and bromocresol purple are available from the Aldrich Chemical Company, Milwaukee, Wis. Preferably, phenol red is used as an aqueous solution containing 0.1 percent weight per volume. Preferably, chlorophenol red and bromocresol purple are used as aqueous solutions containing 0.04% weight per volume.

When the cat litter is prepared by moistening the paper with the liquid phase indicator prior to folding the resulting strips into zig-zag shapes, less pressure is generally required to initially impart a folded memory to the treated paper material. Additionally, when the folds relax, the angular separation between the folds is to a lesser degree than that produced in the dry paper. Additionally, because the separation is to a lesser degree, the folds tend to be more stable and, as the paper dries, tend to retain a smaller angle at the folds than would be accomplished over the same period of time at folds formed in the drier sheet material. Thus, the preferred system for treating the paper with the indicator provides a cat litter comprised of strips having improved "springiness." Hence, the degree of interlocking and intertwining of the strips and the resilient properties of the cat litter can be enhanced.

Although the cat litter (when used to detect FUS) may contain paper strips which have been treated with pH indicator only or with occult blood indicator only, the preferred embodiment is a cat litter containing a mixture of pH indicator-treated strips and occult blood indicator-treated strips. The mixture preferably is a 50—50 mixture of indicator strips; however, the ratio of indicator strips in the mixture may vary according to which pH indicators and occult blood indicators are used. It is also contemplated that cat litter mixtures may also contain untreated paper strips. Regardless of the number or ratio of indicator strips used, it is necessary that the resulting mixture of paper strips be sufficient to provide a noticeable color change of the treated strips, in the presence of alkaline cat urine and/or cat urine containing occult blood. It is contemplated that mixing of the indicator strips may take place at any time during or after their manufacture, including mixing by the cat caregiver prior to use by the cat.

Untreated paper litter strips are preferably also treated with an odor-reducing or neutralizing agent. However, if treated paper strips are used, any odor-reducing or neutralizing agent is preferably present not in the strips themselves, but in the absorbent pad 132 which underlies the paper strips, in order to minimize any chemical interaction between the treated strips and the neutralizing agent. When used in either untreated strips or in the absorbent pad, the odor-reducing or neutralizing agent is preferably present in a quantity sufficient to reduce the level of volatile odorant compounds (primarily ammonia generated by decomposing urine) in the cat litter 10 during the time that it is made available for use by the cat. Preferred odor-reducing agents are disclosed in U.S. Pat. No. 4,938,957, incorporated by reference herein, and are available from Epoleon Corporation, Tokyo, Japan under the product name Epoleon N-100-65-2, and which contains the ingredients zinc phenolsulfonate, malic acid, diethanol amine and water in a composition of 21% weight of solids per volume.

Additionally, the untreated or treated strips or the underlying pad may also be treated with an antibiotic or antibacterial material, such as neomycin. The quantity of antibiotic or antibacterial material is sufficient to retard the growth of any bacterial species present in such use, for a period of time before the cat litter reaches a sanitarily unacceptable condition. The preferred antibiotic is neomycin, in the form of neomycin sulfate, and is obtainable from The Upjohn Company, Kalamazoo, Mich.

The paper material can also be treated with a sizing, such as starch, in an amount sufficient to permit the urine to roll off the strips initially to the bottom of the cat litter, when the cat wets from the top of the litter. The cat urine is then more gradually absorbed by the strips, allowing them to become wetted from the bottom upwards. Consequently, the cat can be kept drier and more comfortable, thereby further encouraging use of the litter by the cat. The amount of sizing applied, however, should not be so great that it prevents the cat urine from being absorbed into the paper, such that it collects at the bottom of the cat box, thereby precluding the cat owner from readily noticing the color changes indicated by alkaline urine or occult blood, for example (and creating a messy disposal problem). The amount of sizing applied also must not be so great as to preclude absorption or adsorption of indicator during the liquid phase treatment of the paper.

As previously indicated, the cat litter 20 is preferably packaged and used in a disposable cat litter box which is convertible between closed and open conditions. Accordingly, the cat box may be compactly stored as a closed receptacle until ready for use, converted into an open receptacle for use by the cat, and then converted back into a closed receptacle for convenient and sanitary disposal.

In one preferred embodiment illustrated by FIGS. 1-3 (disclosed in U.S. patent application Ser. No. 08/125,310 and PCT Patent Application No. PCT/US93/11085, which have previously been incorporated by reference herein), the cat litter box comprises a container 10 which is convertible between a closed condition in which it forms a closed receptacle (FIG. 3) and an open condition in which it forms an open receptacle (FIG. 1). The conversion is accomplished by providing the container 10 with appropriate sets of folding panels and appropriate interconnections therebetween.

The container 10 is initially packaged and supplied in the closed condition, with the cat litter 10 being enclosed within the closed receptacle. When the container 10 is converted to the open condition, the open receptacle confines the cat litter 20 while at the same time permitting a cat access for interaction with the cat litter 20.

The cat may then interact with the cat litter 20 until it reaches a sanitarily unacceptable condition. Once the cat litter 20 reaches a sanitarily unacceptable condition, the container 10 is converted back into the closed receptacle to thereby enclose the sanitarily unacceptable cat litter within the container 10. The container 10, and the sanitarily unacceptable cat litter enclosed therein, may then be disposed of as a unit. In this manner, the often unpleasant and unsanitary task associated with changing cat litter in conventional boxes is eliminated.

The container 10 is made of material which is sufficient strength to function as a self-standing carton in its open condition and of sufficient flexibility to convert between the open and the closed condition. Preferably, the container 10 is made of a paper material so that it is biodegradable and recyclable, and thus environmentally responsible. The container 10 should also be made of a light-weight material, whereby the box's weight and size parameters do not nullify its convenience in connection with disposal.

More preferably, the container 10 is made of corrugated cardboard as this material economically provides the desired characteristics. In the preferred embodiment, the container 10, when empty, weighs approximately one pound, and the completed cat litter box (i.e., the cat litter 20 and the container 10 enclosing the litter) weighs approximately one and one-half pounds. By way of comparison, applicants' testing has proven that if the preferred container 10 was filled with a conventional clay litter, it would weigh approximately from eight to nine pounds. Also by way of comparison, applicants' testing has proven that if the preferred container 10 was filled with "scoopable" clay litter, it would weigh approximately from six to eight pounds. (Applicants note that this comparison may be somewhat conservative because it may actually require a greater volume of clay litter and/or "scoopable" litter to replace the resilient paper cat litter 20.) Applicants contemplate a depth of their fresh, resilient, low-density cat litter of about one and one-half inches, whereas conventional clay kitty litters call for a depth of two inches. In the above described comparative testing, applicants' containers were filled only to a depth of one and one-half inches with, respectively, the fresh cat litter of the present invention and clay cat litter.

Figure 5:
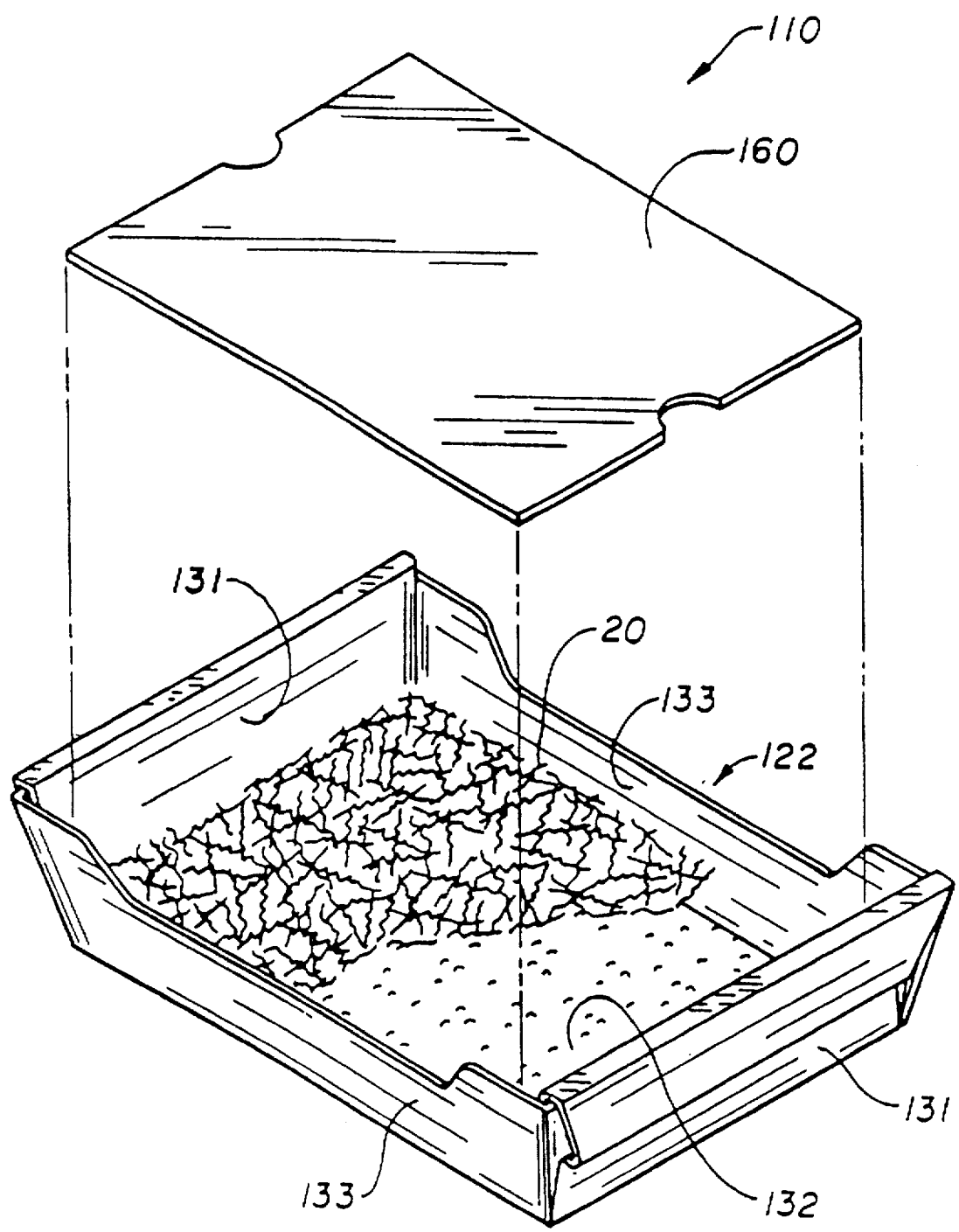
FIG. 5 is a partially exploded and cut-away perspective view of the cat litter box of FIG. 4.
Figure 6:
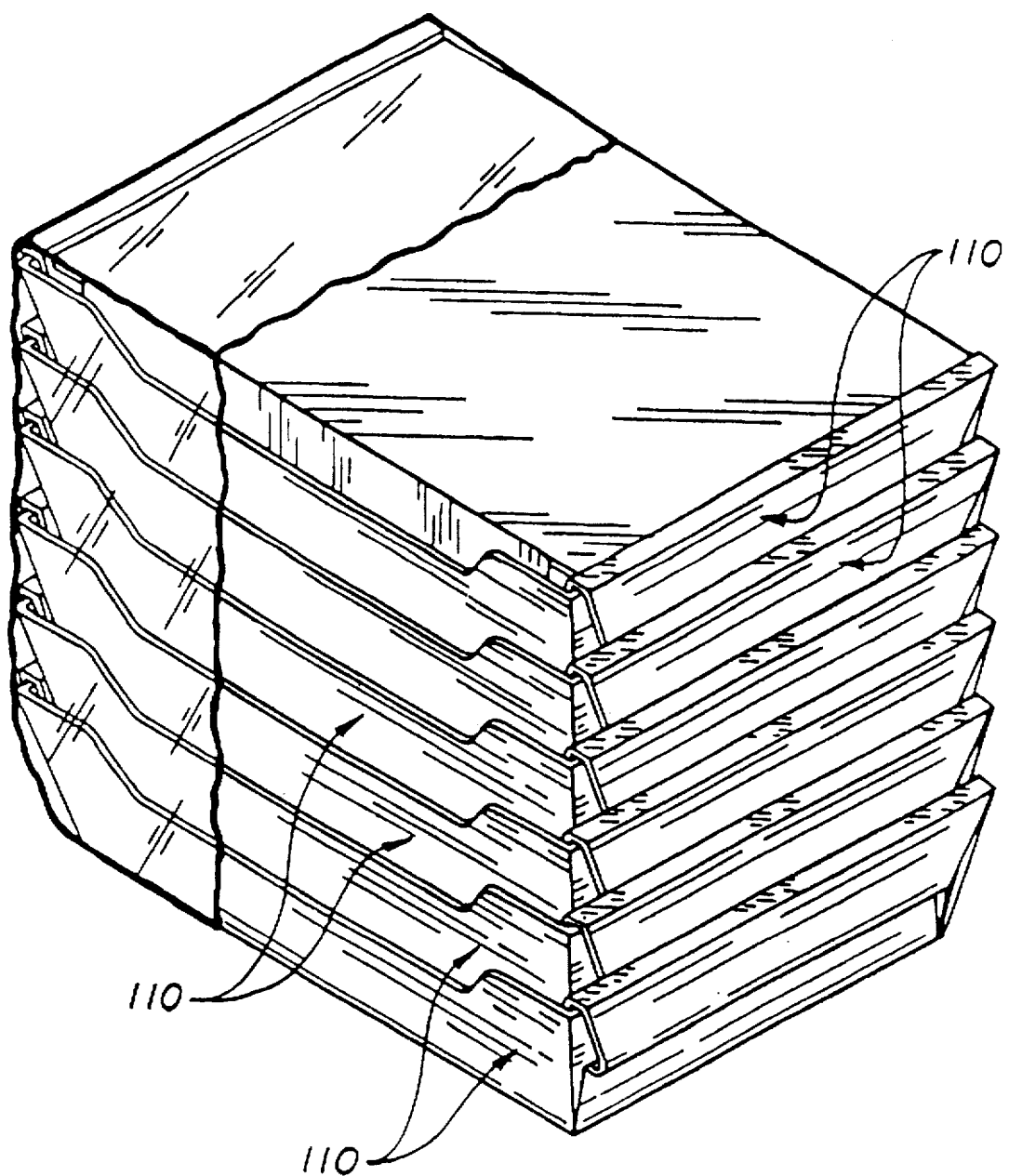
FIG. 6 is a perspective view of a nested stack of six of the cat litter boxes of FIG. 4.

In another preferred embodiment illustrated in FIGS. 4–6 (and disclosed in U.S. patent application Ser. No. 08/125, 310 and PCT Patent Application No. PCT/US93/11085, previously incorporated by reference herein), the shape of the container allows multiple containers to be nestably stacked. In this second preferred embodiment, the length and width of the bottom of a first container 110 fits easily within the open space above the cat litter 20 defined by the portion of the walls extending above the cover panel 160, of a second, lower container 110, whereby the bottom of the first container 110 preferably actually rests upon the cover panel 160 and partially within the walls of the lower container 110 with which it is nested. Thus, while the container 110 may have a height of, e.g., four inches, when the container is nestably stacked in accordance with the invention, the container contributes only about one and three-quarters inch to the total height of a nested stack of such containers.

In this embodiment of the invention, to convert the disposable cat litter box between the open and closed conditions, the user simply removes or replaces top panel 160 within the receptacle formed by panels 131 and 133. When in the closed condition, top panel 160 will be in contact with the cat litter 20, and will resiliently compress cat litter 20 somewhat. The compactability, in conjunction with the stackability and nestability of the preferred cat box, combine to provide unexpected benefits in cost savings and space savings during storage and shipping.

As illustrated in FIG. 4, the preferred embodiment also includes an absorbent, anti-bacterial pad 132 positioned at the bottom of the container 110. The preferred absorbent pad has approximately 28 pound weight, is unlined, and has been treated with a broad-spectrum antibiotic or antibacterial material such as neomycin. The most preferred absorbent paper material 132 is 28 pound Shoksorb with neomycin, available from Kieffer Paper Mills, Inc. Brownstown, Ind. 47220.

The pad is also preferably treated with an odor-reducing or neutralizing agent, including those previously described herein. (Although not specifically shown in these drawings, the cat litter of FIGS. 1–3 also preferably includes an absorptive pad treated with anti-bacterial and odor-neutralizing agents and positioned at the bottom of the container.)

Further, the walls of the preferred, disposable cat litter box are preferably coated with a biodegradable, water-repellant and urine-resistant material. A preferred material is Michelman "42 KR", but other suitable materials are also available from Michelman, Incorporated, Cincinnati, Ohio.

Applicants contemplate that the cat litter of the invention, alone or in conjunction with the preferred disposable cat litter boxes, may be used in the homes of cat owners to monitor feline diseases, particularly FUS, conveniently and inexpensively. Also, applicants contemplate that the cat litter would be advantageous in situations where a large number of cats need to be monitored for FUS, such as at veterinarian offices or kennels, animal shelters and/or pet stores.

What is claimed is:

1. A method of producing a cat litter, for detecting a feline disease which is indicated by a predetermined characteristic of cat urine, which comprises a porous and resilient paper product, said method comprising the steps of:

provviding a web of paper material having a tendency to resist folding and including an indicator selected such that the paper material exhibits a marked color change when wetted with cat urine having the predetermined characteristic;

cutting the web into a plurality of longitudinal strips;

folding said strips transversely into generally zig-zag shapes; and treating the paper material with a sizing, in an amount sufficient to permit the litter to wet from bottom upwards, when a cat urinates on the top of the litter.

2. The method of claim 1, wherein said strips are further permitted to intertwine and interlock to combine and form a mass.

3. The method of claim 1, wherein the feline disease is FUS, the predetermined characteristic of the cat urine is an alkaline pH, and the strips have been treated with a pH indicator selected such that the treated strips exhibit a noticeable color change when wetted with alkaline cat urine.

4. The method of claim 3, wherein the treated strips exhibit a noticeable color change when wetted with alkaline cat urine having a pH at or above about 6.8.

5. The method of claim 3, wherein the indicator is selected from the group consisting of bromocresol purple, chlorophenol red and phenol red.

6. The method of claim 1, wherein the feline disease is selected from the group consisting of FUS and cystitis, the predetermined characteristic of the cat urine is the presence of occult blood in the urine, and the strips have been treated with a blood indicator selected such that the treated strips exhibit a noticeable color change when wetted with cat urine comprising occult blood.

7. The method of claim 1 wherein the indicator comprises a leuco-dye.

8. The method of claim 2, wherein the mass has a density between about 0.01 and 0.100 ounces per cubic inch.

9. The method of claim 1, wherein the paper material is biodegradable.

10. The method of claim 1, wherein the paper material has further been treated with a bacteria-preventing agent in an amount effective to retard the growth of bacteria associated with the cat urine.

11. The method according to claim 1, wherein the providing step further comprises providing an untreated web of paper and treating the web with the indicator.

12. A method as set forth in claim 1 wherein the paper material is made of bleached Kraft paper.

13. A method of producing a cat litter, for detecting a feline disease which is indicated by a predetermined characteristic of cat urine and which comprises a porous and resilient paper product; said method comprising the steps of:

providing a web of paper material including an indicator causing the paper material to exhibit a noticeable color change when wetted with cat urine having the predetermined characteristic of the feline disease and treated with a sizing in an amount sufficient to permit the litter to wet from bottom upwards, when a cat urinates on top of the litter, cutting the web into a plurality of longitudinal strips; and folding said strips transversely into generally zig-zag shapes.

14. A method as set forth in claim 13 wherein the paper material is made of bleached Kraft paper.

* * * * *